United States Patent
Hawker et al.

(10) Patent No.: US 9,260,443 B2
(45) Date of Patent: Feb. 16, 2016

(54) ORGANIC ELECTRONIC DEVICES PREPARED USING DECOMPOSABLE POLYMER ADDITIVES

(75) Inventors: Craig J. Hawker, Santa Barbara, CA (US); Michael Chabinyc, Santa Barbara, CA (US); Sung-Yu Ku, Goleta, CA (US); Christopher Liman, Santa Barbara, CA (US); Shinji Aramaki, Yokohama (JP); Hengbin Wang, Santa Barbara, CA (US); Takaaki Niinomi, Yokohama (JP)

(73) Assignees: The Regents of the University of California, Oakland, CA (US); Mitsubishi Chemical Corporation (JP)

( * ) Notice: Subject to any disclaimer, the term of this patent is extended or adjusted under 35 U.S.C. 154(b) by 563 days.

(21) Appl. No.: 13/333,547

(22) Filed: Dec. 21, 2011

(65) Prior Publication Data
US 2012/0168728 A1    Jul. 5, 2012

Related U.S. Application Data

(60) Provisional application No. 61/429,653, filed on Jan. 4, 2011.

(51) Int. Cl.
| | |
|---|---|
| *H01L 51/46* | (2006.01) |
| *B82Y 30/00* | (2011.01) |
| *C07D 487/22* | (2006.01) |
| *B82Y 40/00* | (2011.01) |
| *H01L 51/00* | (2006.01) |
| *B82Y 10/00* | (2011.01) |

(Continued)

(52) U.S. Cl.
CPC .............. *C07D 487/22* (2013.01); *B82Y 10/00* (2013.01); *B82Y 30/00* (2013.01); *B82Y 40/00* (2013.01); *H01L 51/0007* (2013.01); *H01L 51/0026* (2013.01); *H01L 51/004* (2013.01); *H01L 51/0037* (2013.01); *H01L 51/0046* (2013.01); *H01L 51/0077* (2013.01); *H01L 51/0558* (2013.01); *H01L 51/4253* (2013.01); *Y02E 10/549* (2013.01)

(58) Field of Classification Search
None
See application file for complete search history.

(56) References Cited

U.S. PATENT DOCUMENTS

| | | |
|---|---|---|
| 2003/1022699 | 12/2003 | Shinji Aramaki et al. |
| 2005/0148129 A1* | 7/2005 | Bao et al. ............... 438/197 |
| 2006/0286314 A1* | 12/2006 | Park et al. ............... 428/32.6 |

(Continued)

FOREIGN PATENT DOCUMENTS

| | | |
|---|---|---|
| JP | 2004-247481 | 9/2004 |
| JP | 2008-100993 | 5/2008 |

(Continued)

OTHER PUBLICATIONS

F. Würthner, K. Meerholz, Chem. Eur. J. 2010, 16, 9366-9373.

(Continued)

*Primary Examiner* — Fernando L Toledo
*Assistant Examiner* — Valerie N Newton
(74) *Attorney, Agent, or Firm* — Gates & Cooper LLP (57) ABSTRACT

A method of fabricating an organic device is provided comprising providing a first solution comprising an organic semiconductor or a precursor thereof; a solvent and a decomposable polymer additive, where the polymer additive is heated so that it decomposes into gas. The method is applicable to large scale fabrication of OLEDs, OPVs and OFET devices.

24 Claims, 5 Drawing Sheets

(51) Int. Cl.
*H01L 51/05* (2006.01)
*H01L 51/42* (2006.01)

(56) References Cited

U.S. PATENT DOCUMENTS

2008/0157126 A1* 7/2008 Bertin et al. ............... 257/209
2009/0308458 A1 12/2009 Aramaki et al.

FOREIGN PATENT DOCUMENTS

JP 2010-192891 9/2010
WO WO 2007/126102 A1 11/2007

OTHER PUBLICATIONS

X. Zhan, D. Zhu, Polym. Chem., 2010, 1, 409-419.
A. J. Heeger, Chem. Soc. Rev., 2010, 39, 2354-2371.
J. L. Delgado, P.-A. Bouit, S. Filippone, M Á. Herranza, Nazario Martin, Chem. Commun., 2010, 46, 4853-4865.
S. Günes, H. Neugebauer, N. S. Sariciftci, Chem. Rev. 2007, 107, 1324-1338.
C. Li, M. Liu, N. G. Pschirer, M. Baumgarten, K. Müllen, Chem. Rev. 2010, 110, 6817-6855.
Y.-J. Cheng, S.-H. Yang, C.-S. Hsu, Chem. Rev. 2009, 109, 5868-5923.
A.C. Mayer, S.R. Scully, B.E. Hardin, M.W. Rowell, M.D. McGehee, Materials Today 2007, 10, 28.
Y. Sato, T. Niinomi, M. Hashiguchi, Y. Matsuo, E. Nakamura P. SPIE. 2007, 6656.
Y. Sato, T. Niinomi, Y. Abe, Y. Matsuo, E. Nakamura P. SPIE. 2008, 7052.
Y. Matsuo, Y. Sato, T. Niinomi, I. Soga, H. Tanaka, E. Nakamura, J. Am. Chem. Soc. 2009, 131, 16048.
M. Singh, H. M. Haverinen, P. Dhagat, G. E. Jabbour, Adv. Mater. 2010, 22, 673.
Y. Chang, S. Tseng, C. Chen, H. Meng, E. Chen, S. Horng, C. Hsu, Organic Electronics 2009, 10, 741.
V. Marin, E. Holder, M. M. Wienk, E. Tekin, D. Kozodaev, U. S. Schubert, Macromol. Rapid Commun. 2005, 26, 319.
E. Holder, B. M. W. Langeveld, U. S. Schubert, Adv. Mater. 2005, 17, 1109.
A. R. Murphy and J. M. J. Fre'chet, Chem. Rev. 2007, 107, 1066-1096.
H. N. Tsao, K. Müllen, Chem. Soc. Rev., 2010, 39, 2372-2386.
Y. Yamashita, Sci. Technol. Adv. Mater. 10 (2009) 024313 (9pp).
B. J. Jung, N. J. Tremblay, M.-L. Yeh, H. E. Katz, Chem. Mater., DOI:10.1021/cm102296d.
A. C. Grimsdale, K. L. Chan, R. E. Martin, P. G. Jokisz, A. B. Holmes, Chemical Reviews, 2009, 109, 897-1091.
J. Kido, Y. Okamoto, Chem. Rev. 2002, 102, 2357-2368.
S.-C. Lo, P. L. Burn, Chem. Rev. 2007, 107, 1097-1116.
Y. Shirota, H. Kageyama, Chem. Rev. 2007, 107, 953-1010.
K. Walzer, B. Maennig, M. Pfeiffer, K, Leo, Chem. Rev. 2007, 107, 1233-1271.
X. Chen, Z. Chen, Y. Zhang, Macromolecules, 1991, 24, 5305.
O. Vogl, J. of Poly. Sci., Part A, 1964, vol. 2, 4591-4606.
S. Ito, T. Murashima, H. Uno, N. Ono, Chem. Commun., 1998 1661.
S. Ito, N. Ono, S. Aramaki, JP2008100993.
T. Okujima, Y. Hashimoto, G. Jin, H. Yamada, H. Uno, N. Ono, Tetrahedron 64, 2008, 2405e2411.
S. Aramaki, J. Mizuguchi, Acta Crystallogr E Struct Rep Online 2003, 59, 1556-1558.
J. H. Burroughes, et al., "Light-emitting diodes based on conjugated polymers", Nature, 347, 539-541 (1990).

* cited by examiner

|     | Mn  | Mw   | PDI  | $T_d$ (10%) °C |
|-----|-----|------|------|----------------|
| PC1 | 76K | 125K | 1.64 | 267            |
| PC2 | 76K | 106K | 1.39 | 179            |
| PC3 | 74K | 109K | 1.47 | 173            |
| PC4 | 96K | 166K | 1.73 | 251            |
| BP  |     |      |      | 150-200        |

Figure 6

ORGANIC ELECTRONIC DEVICES PREPARED USING DECOMPOSABLE POLYMER ADDITIVES

CROSS REFERENCE TO RELATED APPLICATIONS

This application claims the benefit of Provisional Patent Application No. 61/429,653, filed on Jan. 4, 2011, which is incorporated by reference herein in its entirety.

FIELD OF THE INVENTION

The invention relates generally to an apparatus and method for producing electronic devices. More particularly, it relates to the use of decomposable polymer additives for producing organic electronic devices.

BACKGROUND OF THE INVENTION

Organic photovoltaics (OPV)[1-7] based on single active layer bulk heterojunction comprising a pair of materials where electron transfer occurs from a donor material to an acceptor material where the pair forms a layer with a higher surface area than a simple flat bilayer structure have been drawing attention because they can be processed from solution at low cost and energy consumption. The most conventional OPV devices consisting of an electron donating polymer such as P3HT and an electron accepting material, such as PCBM, are intensively studied, since they can provide a single active layer bulk heterojunction (BHJ). The morphological structure of blends of polymers is hard to control, but small-molecular OPV system would provide a better control of film morphology. Several concepts have the potential to improve the morphology of OPV devices. One of these is the use of blocking layers to create a so-called p-i-n device. This terminology refers to a structure where the BHJ layer is sandwiched between a pure layer of a dominantly p-type material and a dominantly n-type material. The p and n layers may or may not be electrically doped in this structure. Through the use of convertible materials or orthogonal solvents, these blocking layers can be solution-processed from the same materials in the heterojunction i-layer. Another concept is the ordered heterojunction, in which the donor and acceptor materials form direct paths to the anode and cathode respectively[8] Recently, the use of a spin-cast thermally convertible benzoporphyrin (BP) (FIG. 1 a) has been shown to take advantage of both these concepts.[9,10] This p-i-n device exhibits a power-conversion efficiency of 5.2%, which was successfully demonstrated by spin casting method.[11] However, it is hard to fabricate large areas with spin-casting methods. The alternative processing methods to fabricate larger areas include inkjet printing[12] and slot or blade coating.[13] These methods have worked for polymers such as P3HT[14,15] due to viscous solutions, but small molecule tend to be problematic. More viscous solutions would greatly aid the use of the latter. While adding a polymer additive to the solution to make it more viscous would aid in the use of these methods, the challenge is that the polymer additive cannot diminish the electronic properties of the original materials. A new solution processing method that utilizes a degradable polymer additive would be a great benefit to device fabrication. Similarly, the decomposable polymer additives can be applied to the fabrication of various other organic electronics devices, including but not limited to OFET, OLED, photodetector, sensor and integrated circuit. For example, many polymer, oligomer, dendrimer and small molecule semiconductors had been developed for OFET and OLED devices by printing or coating process.[16-24] Again, certain solution viscosity is generally required for the printing or coating process which could be difficult to achieve from the semiconductor solution especially when the semiconductor or semiconductors are small molecules, oliogmers or dendrimers. A decomposable polymer additive which increase the solution viscosity at the coating step and which then is removed later by annealing could dramatically improve the film quality so as the device performance.

Figure 1:
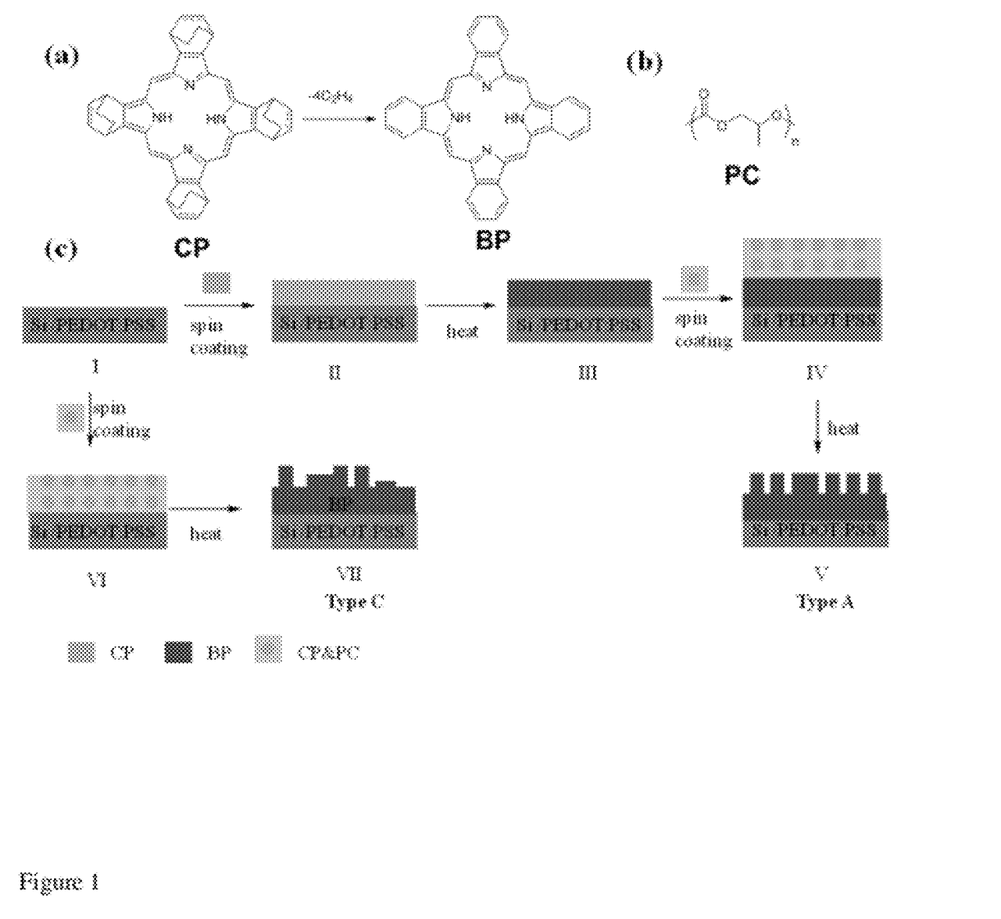
FIG. 1 shows (a) Transformation of BP precursor (CP) to benzoporphyrin (BP) during annealing; (b) polypropylene carbonate; (c) Two types of BP film preparation.

Poly(propylene carbonate) (PC) (FIG. 1b) derived from carbon dioxide and propylene oxide has attracted practical interest with respect to the $CO_2$ fixation and biodegradability.[25] PC also exhibits high transparency and superior mechanical strength. The carbonate linkage in the backbone of PC results in a relatively low thermal decomposition temperature (Td), potentially limiting its practical applications. But from another point of view, the lower Td and decomposing properties could be beneficial for certain applications. Novomer, Inc. has claimed that its synthetic procedure is able to produce PC which decomposes more uniformly at lower temperatures with extremely low residue left after the annealing process. TGA analysis shows that PC can degrade 100% completely above 200° C.

BRIEF SUMMARY OF THE INVENTION

The present invention overcomes the foregoing drawbacks. In contrast to the above-described One advantage of using decomposable binders/polymers instead of washable polymer additives with organic semiconductors in OLED and other electronic devices is that the majority of conventional organic semiconductors are soluble in the solvents used to wash away the polymer additives. Thus in attempting to wash away most of the washable polymer additives from the device layer, some of the organic semiconductor will also be removed, thereby lowering overall device efficiency/performance. Accordingly, in one embodiment, the polymer additives are removed from the device layer without employing any washing steps to remove the polymer additives.

We incorporated a degradable poly(propylene carbonate) (PC) polymer additive into the BP precursor solution and showed increase solution viscosity and improve processability of solar cell devices. This allows for greater flexibility in film preparation techniques such as slot coating, blade coating, inkjet printing, dip coating, and screen printing, which are processes more suited to large area fabrication. For instance, such areas considered 'large' can include, but are not limited to areas of 0.1 square meters or larger. The disclosed PC polymer additive used in the preparation of benzoporphyrin/fullerene solar cells does not diminish efficiency. The PC fully decomposes on annealing and does not change the crystal structure or texturing of BP. Furthermore, the addition of the PC causes a more nanostructured morphology to form in the BP, allowing a bulk heterojunction to form between the BP and the PCBNB which is added afterwards. Devices with this bulk heterojunction exhibit comparable performance to the previously used method of mixing the BP and PCBNB to create a bulk heterojunction. Another advantage of using the former method is that the size of the BP crystallites and gaps is not determined by the acceptor, making the method more extendable to different acceptors.

In one embodiment, a method of fabricating an organic device is provided comprising providing a first solution comprising an organic semiconductor or a precursor thereof; a solvent and a decomposable polymer additive, casting said first solution, and removing at least 80% of the polymer additive by decomposing the polymer additive into volatile small molecules.

In another embodiment, the above mentioned polymer additive of paragraph [008] is decomposed by radiation or heating the casted first solution to a temperature at or above the decomposition temperature of the polymer additive. In yet another embodiment, the decomposition temperature of the polymer additive is 400 deg. C. or lower.

In another embodiment, the above mentioned polymer additive of paragraph [008] is either a linear or block copolymer.

In yet another embodiment, the polymer additive of paragraph [008] is selected from the group consisting of polyethers, polyacrylates, polyisocyanurates, aliphatic polycarbonates, polyethylene carbonates, polyesters, polysulfones and polystyrene or poly (.alpha. methyl styrene).

In another embodiment, the polymer additives of paragraphs [008] and [011] is selected from the group consisting of poly carbonate, poly-phenylene oxide, poly (methyl methacrylate), poly (4-vinyl phenol), poly (4-vinyl pyridine), polyaldehyde, and poly(lactide-co-glycolide).

In yet another embodiment, the above poly carbonate has the following structure:

where R is bivalent and R is an alkanediyl, alkenediyl or alkynediyl group with less than 10 carbon atoms.

In another embodiment, the above organic semiconductor or a precursor thereof of paragraph [008] is a compound with a molecular weight less than or equal to 2000.

In yet another embodiment, the organic semiconductor precursor of paragraph [008] is either is 1,4:8,11:15,18:22,25-tetraethano-29H,31H-tetrabenzo[b,g,l,q]porphyrin. or one of the following compounds:

Or

Where Y1-Y4 are H or alkyl group; R1-R4 are H, alkyl group or aryl group, F, or Cl; Z1a-Z4b are H, or alkyl group; and M is bivalent metal.

In another embodiment, the device is coated with benzoporphyrin prior to casting said first solution.

In yet another embodiment, a composition is provided comprising an organic semiconductor, or a precursor thereof, and a polymer additive, wherein at least 80% of the polymer additive is capable of decomposing into gas upon heating, wherein the polymer additive is 1,4:8,11:15,18:22,25-tetraethano-29H,31H-tetrabenzo[b,g,l,q]porphyrin, or one of the following compounds with the following formulas:

or

-continued where Y1-Y4 are H or alkyl group; R1-R4 are H, alkyl group or aryl group, F, or Cl; Z1a-Z4b are H, or alkyl group; and M is bivalent metal.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Results and Discussion

The term "decomposable polymer additives" as used in this application refers to a group of polymers of which 1) increases the viscosity of other polymers in solution, and 2) decomposes by 80% of its initial weight into decomposing the polymer additive into volatile small molecules, or gas, within 2 hours, when heated at a temperature of 400 deg C. or lower.

Decomposable polymer additives that can be used with OLEDs, OPVs and OFET using the methods of the instant disclosure are, but not limited to, compounds such as a polymer selected from polyester, polyether, polycarbonate, polystyrene, poly(.alpha.-methylstyrene) polyacrylate or polymethacrylate; polyaldehyde, and poly(lactide-co-glycolide), or various combinations thereof. These decomposable binder compounds can be either linear or branched in structure.

The decomposable polymer additive compound is decomposed by heating or exposure to radiation with an associated reduction in molecular weight to give small volatile molecules with molecular weights in the range of 20 to 2,000 amu, preferably 20 to 200 amu. The amount of decomposable polymer additive on the device left after decomposition should be from not more than 30%; more preferably no more than 20%, most preferably no more than 10%. The percentage of binder remaining on the device could be determined by methods known to those of skill in the art, such as, but not limited to, thermal gravimetric analysis, XPS and infra-red spectroscopy.

Suitable linear decomposable polymer additives are polyethers such as poly(propylene oxide), polyacrylates such as poly(methyl methacrylate), aliphatic polycarbonates e.g., poly(propylene carbonate), poly(ethylene carbonate), polyesters, polysulfones, polyaldehyde, poly(lactide-co-glycolide) and polystyrene or poly (.alpha. methyl styrene). The decomposable linear polymer additive will preferably be uniformly dispersed within the matrix (i.e. the benzoporphyrin compound) in nanometer scale domains.

Photochemical labile polymer additives can be decomposed by exposure of the composition to suitable radiation to cause photodecomposition. Such conditions are known to those of skill in the art. Thermally decomposable polymer additives are decomposed by heating the composition to a temperature at or above the thermal decomposition temperature of the polymer. (e.g., about 50-300 degree. C.).

In one embodiment, at least 80%, preferably, at least 85%, and most preferably at least 95% of the polymer additive should decompose into gas, leaving some residue behind (i.e. carbon). Polymer additives can be selected with decomposition temperatures less than 300 deg, C; preferably, less than 250 deg. C.; more preferably less than 200 deg. C. The selected decomposable polymer additive can decompose into gas in less than 5 hours; preferably less than 1 hour, more preferably less than 20 minutes.

The selected decomposable polymer additive can be stable at below 50 degree C., preferably 100 degree C. The selected decomposable polymer additive will have a molecular weight of at least 10K Dalton or higher.

In one embodiment, the decomposable polymer additive will be selected so that it can be fully dissolved in the solution used to dissolve the organic semiconductor compound.

In one embodiment, the decomposable polymer additive decomposes to volatile fragments which diffuse out of the matrix (for instance, benzoporphyrin) leaving voids behind. The pore size in the matrix will be generally the same size as the size of the domains of the decomposable polymer additive and the pore size can be altered by varying the molecular weight, nature and loading of the decomposable polymer additive.

In another embodiment, if the polymer additive disappears at low temperature, such as during the device dry process, voids may not be left behind.

An example of a decomposable polymer additive compound is a poly carbonate with the following molecular structure:

where R is bivalent and R is an alkanediyl, alkenediyl or alkynediyl group with less than 10 carbon atoms.

In the preferred embodiment, R is an alkanediyl group. Other Examples of Decomposable Polymer Additive that can be Utilized with OLEDs, OPVs and OFETS:

Polyaldehydes with the following structure, either end capped or not, n=0-12.

Thermal gravimetric analysis under Ar (heating rate 10° C./s) showed that commercial paraformaldehyde decomposes completely between 132° C. to 156° C.

Polyacetaldehyde was synthesized according to the literature procedure[26],

Thermal gravimetric analysis under Ar (heating rate 10° C./s) showed it decomposes completely between 90° C. to 95° C.

Poly(lactide-co-glycolide) with the following structure, m, n=0-1, m+n=1.

Thermal gravimetric analysis under Ar (heating rate 10° C./s) below showed commercial Poly(lactide-co-glycolide) Mw=40-75 k, m=n=0.5 starts to decompose around 220° C.

Figure 6:
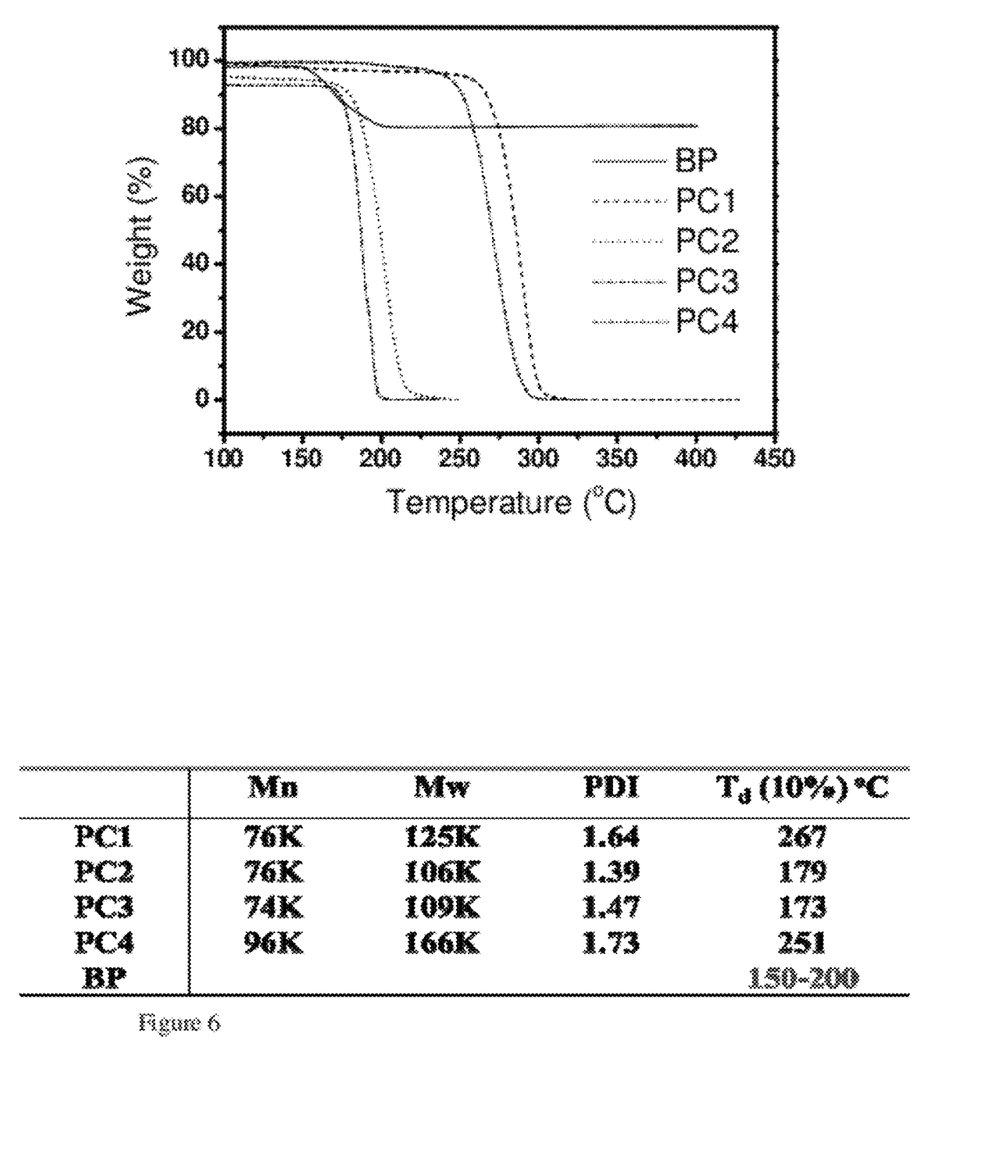
FIG. 6 shows the decomposition temperatures of various polycarbonate polymer additives.

Decomposition temperatures of four polycarbonate polymer additive samples PC1-PC4 from Novomer Inc. (Waltham, Mass., U.S.A) are shown in FIG. 6. Here it is shown that depending upon the polycarbonate structure, they start to decompose between 170 deg. C. to 250 deg. C. and completely decompose between 220 deg. C. to 300 deg. C. (decomposition temperatures obtained from thermogravimetric analysis under Ar gas with heating rate of 10 deg. C./minute).

"Organic semiconductor" to be used alone or mixed with the polymer additive compound for OPV, OFET, and OLEDs devices include, but are not limited to, "small molecule" (for instance, molecules with a molecular weights below 2000) semi-conductor compounds such as benzoporphyrin (BP) or precursors thereof, or other porphyrins or phthalocyanines. More specifically, example of the precursor of BP is show as follows (other precursors of BP are described in references 27-29):

Where Y1-Y4 are each independently H or alkyl group; R1-R4 are each independently H, alkyl group or aryl group, F, or Cl; Z1a-Z4b are each independently H, or alkyl group; and M is bivalent metal. These alkyl groups are those which have less than 6 carbon atoms, such as, methyl, ethyl, propyl groups. Examples of the metal are Zn, Cu, Ni, Co, Mg, etc.

Polymer/conjugated polymers that could also be use as the "organic semiconductor" alone or mixed with the binder include, but are not limited to, P3HT, MEH-PPV, PBTTT, PCDTBT, and PDBTTT (see Chemical Society Reviews, 39, 2354 (2010) for P3HT, MEH-PPV, PBTTT, PCDTBT; and Chem. Commun. 2010, 46, 4853-4865 for PDBTTT).

"Organic semiconductors" to be used with OTFTs, in addition to the above list, also include C60 and its derivatives such as PCBNB, PCBM, SIMEF[11], and the C70, C76, C80 and C84 based versions of these.

In another embodiment, more than one type of the above named organic semiconductor compounds can be mixed together with one or more types of binder compounds.

Compounds to be used as the "second compound" for OPV devices include, but are not limited to, C60 and its derivatives such as PCBNB, PCBM, SIMEF, and the C70, C76, C80 and C84 based versions of these.

A "first solution" comprises a first compound (or 'organic semiconductor") and/or "polymer additive", and any solvent capable of dissolving both of the aforementioned and can include any other additives. Examples of other possible additives are surfactants to control coating property, anti-oxidizing agents, high boiling point compounds to control phase separation, such as, diiodeoctane, octanedithiol, etc. Solvents to be used here are known to those of skill in the art and can include, but are not limited to, chloroform, 2-chloroethanol, toluene, chlorobenzene, 1,2-dichlorobenzene and any combination thereof. For instance in certain applications two or more solvent combinations may be use compared to using only a single solvent type. A person of skill can assess whether any particular solvent or combination thereof is better suited to any particular combination of organic compound and binder, and for the actual method used to fabricate the device.

The percentage ratio of polymer additive to organic semiconductor in a solvent can be between 1:99; 5:95; 20:80; 30:70; 40:60; 50:50; 60:40; 70:30; 80:20; 100:1. The ratio to be selected varies depending upon the combinations of the polymer additive and organic semiconductor types; the solvent; and the desired final viscosity.

A "second solution" comprises the 'second compound" and any solvent capable of dissolving this second compound and can include other additives. A person skill in the art can determine which solvents would work best with this selected 'second compound'.

The preferred viscosity range or value of the first compound in a solvent so that the first compound can be effectively deposited on any given substrate can vary according to the device coating method adopted. For instance, the viscosity can be at least 1 cp at 25 deg. C.; but for coating methods like die coating and gravure coating, more viscous ink (greater than 15 cp) is preferable. Accordingly, a suitable polymer additive, at a suitable ratio of polymer additive to first compound/organic conductor will be added to the first solution to achieve the desired viscosity. In one embodiment, the polymer additive produces a larger viscosity value of the first solution than that of the first solution without the polymer by at least 0.2 cps.

BP is used for the donor layer in the heterojunction device structure due to its promising properties, such as high hole mobility and solution processibility. This present work features nanostructured BP morphology fabricated from a PC polymer additive and BP precursor solution. BP precursor, a soluble CP molecule (1,4:8,11:15,18:22,25-tetraethano-29H, 31H-tetrabenzo[b,g,l,q]porphyrin) is thermally converted to a highly insoluble, crystalline tetrabenzoporphyrin (BP) donor, shown in FIG. 1(a). To study the effect of the PC polymer additive on BP morphology, we prepared two types of BP samples (Type A and Type C films) shown in FIG. 1(c) For Type A, a solution of the donor precursor CP is first spin-coated on the glass/ITO/PEDOT:PSS electrode to form the CP layer (sample II) and is thermally converted to the donor BP at 180° C. to form a donor p-layer (sample III). In the second step, we added degradable PC polymer additive (0.25 wt %) into CP solution (0.75 wt % in chloroform and 2-chloroethanol). Then a homogeneous mixture of CP and PC polymer additive is spin-coated to achieve sample IV. The annealing process of sample IV is crucial since CP is converted in situ to BP at 180° C. and PC polymer additive can decompose completely above 200° C. Therefore, the sample IV was heated at 180° C. and raised to 200° C. to remove the PC polymer additive (yielding sample V). Type C has the same preparation procedure as type A but without the underlying first BP layer. To examine BP morphology, we used top-down view and cross-section SEM to observe the BP film with and without the PC polymer additive. We also used 2-D grazing incidence wide angle X-ray scattering (GIWAXS) to study BP crystal structure and texture.

| BP types | Device structure |
|---|---|
| A | PEDOT/BP/CP&PC |
| B | PEDOT/CP |
| C | PEDOT/CP&PC |
| D | PEDOT/BP/CP |

Figure 2:
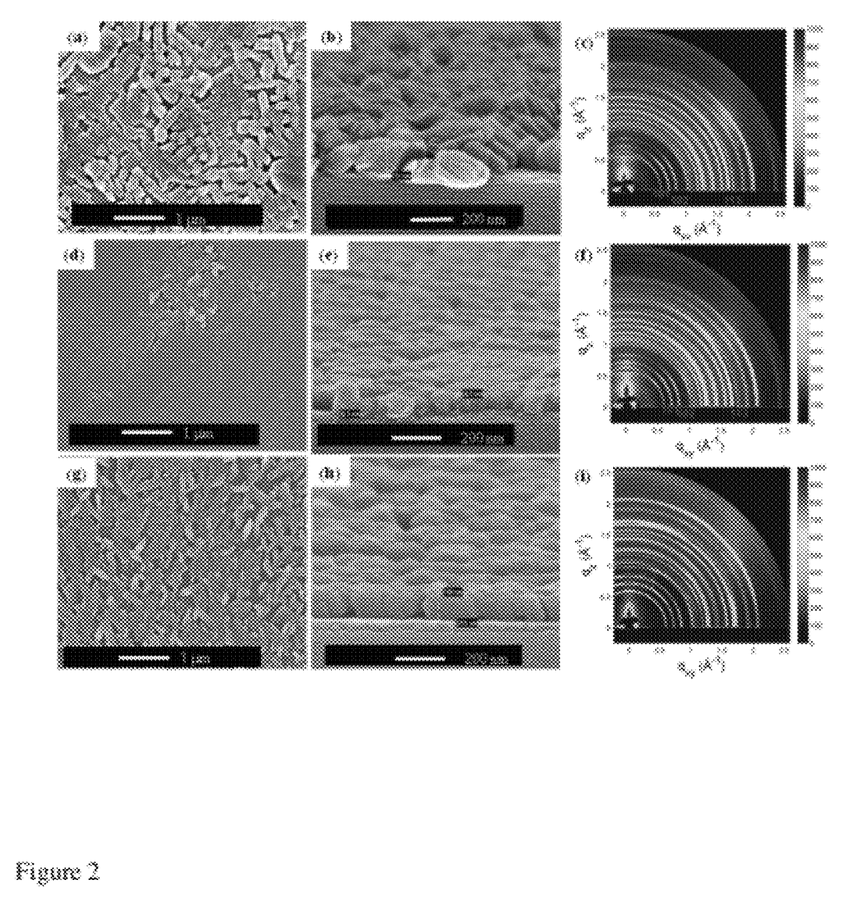
FIG. 2 shows Sample A (PEDOT/BP/CP&PC), sample B (PEDOT/CP) and sample C (PEDOT/CP&PC) after thermal annealing process. CP transform to BP and PC degrade after thermal annealing. (a) top view of sample A; (b) cross-section of sample A; (c) 2-D GIWAXS of sample A; (d) top view of sample B; (e) cross-section of sample B; (f) 2-D GIWAXS of sample B; (g) top view of sample C; (h) cross-section of sample C; (i) 2-D GIWAXS of sample C.

It was found that the addition of the PC polymer additive does not affect the crystal structure and texturing of BP, which is known to be monoclinic.[30] Films of CP (type B) and BP/CP:PC (type A) (FIG. 1c) were examined with 2-D grazing incidence wide angle X-ray scattering (GIWAXS) after annealing. Both the radii of the rings and the texture in the 2-D data were the same for both types and fit the known crystal structure (FIG. 2(c) and (f)). GIWAXS was also done on these types of films while annealing in situ, and the progression of the crystal structure from that of CP to that of BP was found to be the same for both types.

It was also found that the addition of the PC polymer additive does affect the morphology of the resulting BP film, creating a nanostructure that could be beneficial for bulk heterojunction solar cells. Films of type A consisting of PEDOT/BP/CP:PC were annealed and examined under SEM and it was found that the vast majority of the surface is made up of rectangular BP columns as shown in the top-down view of FIG. 2(a). As shown in the cross-section view of FIG. 2(b), each BP column has dimensions of about 100 nm wide and 150 nm tall. In contrast, a single film of BP without PC (type B) didn't show the same morphology as films of type A. These films show two different types of crystal packing, consisting of large flat crystals in the majority and some smaller vertical structures in the minority (FIG. 2(d) and (e)). Films of type D consisting of PEDOT/BP/CP also shows this morphology, but with a slightly more ordered and uniform crystallite packing, as shown in the supporting information. Due to the large flat crystals and fewer gaps, this morphology is good for an electron blocking or p-layer.

We conjecture that the reason for the difference in morphology is that during the annealing process, CP transforms to BP with 20% weight loss, but films of type A transforms with as high as 40% weight loss because it contains PC. The weight loss of type A films not only make them thinner, but also causes them to contract and reorganize. The reorganizing interaction produces ordered polycrystalline BP with some gaps between each crystallite. When the gaps between the crystallites are filled with acceptor material, the morphology forms a bulk heterojunction, or i-layer. The feature size is larger than that of the commonly used bulk heterojunction made by spin coating a mixture of CP and a fullerene such as PCBNB, which results in the BP forming columnar nanostructures about 20 nm in width.[11]

Films of CP:PC without an underlying BP layer (type C) were found to have a different crystal texture and morphology than the previously mentioned films. GIWAXS after annealing showed that the radii of the rings was the same as in the previous samples, meaning that the crystal structure is still the same, but the texture is different (FIG. 2(i)). The 101 and 002 rings are most intense on the qz axis of the figure, indicating that these unit cell directions are orthogonal to the substrate in many crystallites. Since the 101 and 002 directions are orthogonal to the b-axis of the unit cell (010), this means that for a large fraction of crystallites, the b-axis is oriented parallel to the substrate. It has been suggested that the b-axis of BP may have better hole mobility than the a- and c-axes due to π-π stacking. For solar cell devices, then, it is desirable for the b-axis to be orthogonal to the substrate for improved charge transport. However, for TFTs it is desirable for the b-axis to be parallel to the substrate, and type C films may be more useful in this case. In comparison, in samples of type A and B, there is a wider range of crystallite orientations. The morphology of type C films consists of large rectangular columns with a great deal of gaps in between. Each BP column is approximately 300 nm in width and 100 nm in height as shown in FIG. 2(g) and (h). In addition to the GIWAXS data, this also suggests that the long direction of the crystallites is the b-axis. Overall, the data shows that for BP films made with the PC binder, the morphology and crystal texture is affected by whether the base layer is PEDOT or PEDOT/BP. A base layer of PEDOT/BP results in much better crystal coverage as well as smaller crystals that make a better bulk heterojunction.

As the nanostructured BP morphology in type A films (PEDOT/BP/CP&PC) can act as an i-layer, we fabricated a variety of devices with type A films, and compared them to the more common preparation method with type B films (PEDOT/CP) and an i-layer made by spin-coating a mixture of CP and PCBNB. The fabrication method of type A OPV devices is as follows: A solution of the donor precursor CP is first spin-coated on the glass/ITO/PEDOT electrode and is thermally converted to the donor BP at 180° C. to form a donor p-layer. The second layer was spin-coated with a homogeneous mixture of PC polymer additive and CP. Under a two step annealing process at 180° C. and 200° C., the nanostructured BP is formed. Then a layer of PCBNB is spin-coated to fill in the gaps and create an interdigitated i-layer. For type B devices, the second layer is a mixture of CP and PCBNB instead, which forms an i-layer with a smaller feature size. An aluminum electrode is coated in a vacuum to complete the device.

In another embodiment, it is possible to use in these devices other known precursor forms of BP instead of CP.

Films utilizing the bulk heterojunction morphology created as a result of the PC polymer additive can be used to make effective solar cells with certain advantages. The efficiencies of solar cell devices (Table 1) made with type A films which utilize the PC polymer additive (Device A2, 1.35%) were only slightly worse than those of devices with the commonly used bulk heterojunction and without PC (Device B1, 1.54%). One advantage of Device A2 is that the size of the crystallites and gaps in the CP:PC layer is not determined by the acceptor, unlike in Device B1. This makes our method of using PC to create the bulk heterojunction more extendable to different acceptors which may not form a good morphology with BP when deposited at the same time in a mixture. Oddly enough, when an n-layer consisting of PCBNB is added to device B1, the efficiency actually goes down (Device B2, 1.34%), possibly because this spin-coating this layer causes the PCBNB in the i-layer to dissolve, and the total thickness of the device goes down. This does not happen for our type A devices.

The idea of using both the larger and the smaller feature size bulk heterojunctions was also found to have some merit. When a layer of BP:PCBNB was spun on top of the film in Device A2, the efficiency increased slightly (Device A4, 1.43%). The morphology is that of smaller columnar nanostructures on top of larger rectangular crystallites (see S.I.). It was also found that devices with the CP:PC layer spun from chlorobenzene:chloroform were more efficient than those spun from chloroform:chloroethanol. However, the morphology of the two in SEM looked the same (see S.I.)

We know that the insulating PC polymer additive could easily diminish device efficiency and hole transport properties. However, the Jsc of device A2 and A4 can reach 5.1 mA/cm2, which is comparable to the Jsc of device B1 and B2. It indicates that after the annealing process, there is no residue from the PC polymer additive in the BP film. We successfully demonstrated that the addition of PC polymer additive not only has the potential to extend processability to larger dimensions/areas but also result in comparable device properties.

TABLE 1

OPV device data

| Type | Device Structure | $V_{oc}$ [V] | $J_{sc}$ [mA/cm$^2$] | FF | Eff (%) |
|---|---|---|---|---|---|
| Device A1 | PEDOT/BP/BP:PC(CL:CE)/ PCBNB/Al | 0.57 | 4.33 | 0.46 | 1.12 |
| Device A2 | PEDOT/BP/BP:PC(CB:CL)/ PCBNB/Al | 0.54 | 5.15 | 0.48 | 1.35 |
| Device A3 | PEDOT/BP/BP:PC(CL:CE)/ BP:PCBNB/Al | 0.60 | 4.67 | 0.42 | 1.19 |
| Device A4 | PEDOT/BP/BP:PC(CB:CL)/ BP:PCBNB/Al | 0.55 | 5.12 | 0.51 | 1.43 |
| Device B1 | PEDOT/BP/BP:PCBNB/Al | 0.58 | 5.48 | 0.49 | 1.54 |
| Device B2 | PEDOT/BP/BP:PCBNB/ PCBNB/Al | 0.41 | 5.45 | 0.60 | 1.34 |

The following OPV/solar cell devices were fabricated by Mitsubishi Chemical, and incorporate a different fullerene derivative as well as a buffer layer to increase device performance. They further show that the use of the PC polymer additive can be used to make successful solar cell devices.

EXAMPLE 1

Fabrication of Device A

Figure 3:
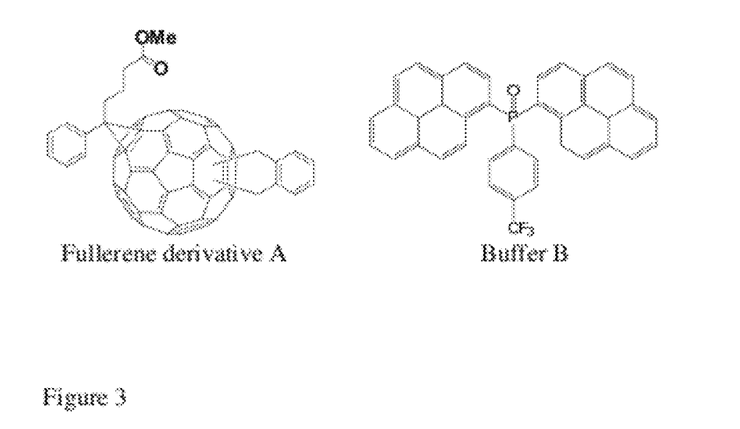
FIG. 3 shows the molecular structure of fullerene derivative A and buffer B.

We fabricated device A using the compound in FIG. 3 according to the following procedure. The ITO layer on a glass substrate was 145 nm thick with a sheet resistance of 8 ohms/square. The 5 mm wide stripe pattern on the ITO layer was etched by conventional photolithographic techniques. Prior to the formation of the buffer layer, the patterned ITO glass was ultrasonically cleaned using surfactant, rinsed in deionized water and finished with an air plasma treatment. The PEDOT:PSS (Clevios AI4083) layer was formed on the ITO substrate by spin coating (3,000 rpm) from an aqueous dispersion to give a smooth, 30 nm thick film. The coated PEDOT:PSS layer was baked for 10 minutes at 120° C. in air and annealed for 3 minutes at 195° C. in a nitrogen glove box just prior to use. The solution of 1.0 wt % CP and PC (3:1 weight ratio) in a mixture of chloroform:chlorobenzene (1:1 weight ratio) was spin-cast (1500 rpm) on the PEDOT:PSS layer in a nitrogen glove box. Thermal conversion of the CP to BP was then carried out at 195° C. for 20 minutes, and then at 225° C. for 20 minutes to ensure the decomposition of the PC. Fullerene derivative A in FIG. 3 was used as an acceptor. Fullerene layer was spin-cast (3000 rpm) from the toluene solution (0.65 wt. % fullerene derivative A). After drying the thus coated layers for 10 minutes at 120° C., the substrate was transferred from glove box to a vacuum chamber without being exposed to air. Evaporation of buffer B in FIG. 3 was carried out at a pressure of about $4\times10^{-4}$ Pa. Deposition rate was typically 0.04 nm/s. After the deposition of buffer B layer, the top electrode (Al) was successively deposited with a metal shadow mask, which defines 5 mm stripe pattern perpendicular to the ITO stripe. The device A was performed the thermal treatment after top electrode evaporation at the temperature from 150° C. to 205° C. and then was subject to I-V measurement under both dark and irradiated condition. Current-voltage sweeps were taken with a Keithley 2400 source measurement unit controlled by a computer. Light source for power conversion efficiency, we used a solar simulator system (WACOM ELECTRIC CO., LTD.), AM1.5G, with intensity of 100 mW/cm2. The result was summarized in Table 2.

EXAMPLE 2

Fabrication of Device B

Device B was fabricated in a same way as device A except the process of coating BP layer. BP layer was formed on the PEDOT:PSS layer by spin coating (1500 rpm) from 0.5 wt % CP solution in a mixture of chloroform:chlorobenzene (1:2 weight ratio). Thermal conversion of the CP to BP was then carried out at 195° C. for 20 minutes in a nitrogen glove box. The solution of 1.0 wt % CP and PC (3:1 weight ratio) in a mixture of chloroform:chlorobenzene (1:1 weight ratio) was subsequently spin-cast (1500 rpm) on the thus coated layer in a nitrogen glove box. After that, the device B was fabricated in the same way as device A. The OPV characteristics of device B was summarized in Table 2.

EXAMPLE 3

Fabrication of Device C

Device C was fabricated in a same way as device B except the solution of CP and PC mixture. The solution for device C was 1.0 wt % CP and PC (3:1 weight ratio) in a mixture of chloroform: 2-chloroethanol (2.5:1 weight ratio). The OPV characteristics of device C was summarized in Table 2.

EXAMPLE 4

Fabrication of Device D

Device D was fabricated in a same way as device B except the solution of CP and PC mixture. The solution for device C was 2.0 wt % CP and PC (0.6:1.4 weight ratio) in a mixture of chloroform:chlorobenzene (1:1 weight ratio). The device D was performed the thermal treatment after top electrode evaporation at the temperature from 150° C. to 180° C. The OPV characteristics of device D was summarized in Table 2.

TABLE 2

Photovoltaic characteristics of device A, B, C, D

|  | Voc [V] | Jsc [mA/cm2] | FF | PCE [%] |
|---|---|---|---|---|
| Device A | 0.71 | 5.5 | 0.63 | 2.4 |
| Device B | 0.74 | 6.2 | 0.65 | 3.0 |
| Device C | 0.68 | 3.9 | 0.60 | 1.6 |
| Device D | 0.64 | 4.4 | 0.62 | 1.8 |

Solution Viscosity Measurement

We measured the viscosity for the solution of CP and PC mixture and the solution of CP and fullerene derivative B.

Figure 4:
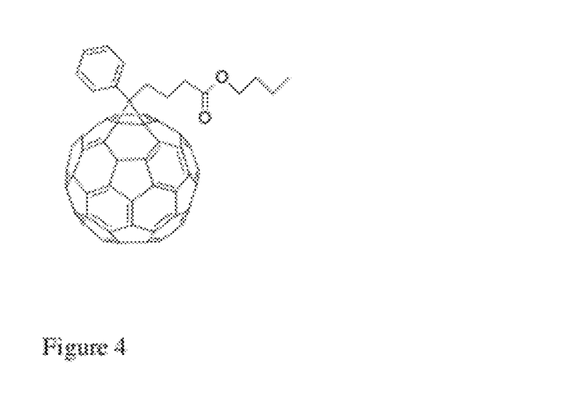
FIG. 4 shows the molecular structure of fullerene derivative B.

Solution A contained 2.0 wt % CP and PC (0.6:1.4 weight ratio) in a mixture of chloroform:chlorobenzene (1:2 weight ratio). Solution B contained the fullerene derivative B (FIG. 4) instead of PC. We used viscometer RE-80L (TOM SANGYO CO., LTD.) The viscosity of solution A and B were 1.6 cp and 0.8 cp at 25° C., respectively. The viscosity of the solution including PC is higher than the one of the solution including fullerene derivative B. Applying PC into the solution is effective to adjust the viscosity of the solution.

Advantages of Devices Fabricated as a Result of Decomposing the Polymer Additive Compared to Washing Away the Polymer Additive It is expected that electronic devices, whether OLED, OPV or OFET, made as a result of decomposing the polymer additive are more efficient compared to devices where the polymer additive is removed by washing because most organic semiconductors are soluble to some degree in the solvents typically used to wash away washable polymer additive, thereby resulting in lower amounts of the organic semiconductor remaining on the device, or poor film quality; thereby resulting in decreased performance.

Examples of Organic Thin Film Transistors (OTFTs) Made Using Decomposable Polymer Additive Thin film transistors were fabricated on silicon substrates with 150 nm of thermal oxide as a dielectric layer. The substrates were sonicated in acetone and isopropanol and plasma cleaned. On some devices, an additional 140 nm dielectric layer of polyvinylphenol (PVP) was spin coated on the substrate at 2000 rpm, and annealed at 100° C. for 30 seconds and then 200° C. for 10 minutes. Solutions of the semiconducting materials were made in a glovebox: A) 7 mg/mL of BP precursor in 2:1 chlorobenzene:chloroform; B) 7.5 mg/mL of BP precursor and 2.5 mg/mL of PC in 2:1 chlorobenzene:chloroform; C) 30 mg/mL of PCBM in chlorobenzene; D) 24 mg/mL of PCBM and 6 mg/mL of PC in chlorobenzene. These solutions were filtered and spin-coated in a glovebox at 1500 rpm. The films were annealed at 200° C. for 20 minutes. To make source and drain contacts, 90 nm of gold for the BP p-type devices or aluminum for the PCBM n-type devices was thermally evaporated using a mask. To make the gate contact, the bottoms of the substrates were scratched and silver paint used to make contact with the silicon. A probe station was used to obtain device characteristics.

Results

TABLE 3

| Device type | Device structure | Charge Carrier Mobility ($cm^2/V\ s$) | Threshold Voltage (V) | On/Off Ratio |
|---|---|---|---|---|
| A | $SiO_2$/BP/Au | $4.5 \times 10^{-3}$ | −5 | $10^2$ |
| B | $SiO_2$/BP/BP + PC/Au | $1.0 \times 10^{-2}$ | 11 | $10^{1.5}$ |
| C | $SiO_2$/PVP/PCBM/Al | $4.7 \times 10^{-5}$ | 26 | $10^2$ |
| D | $SiO_2$/PVP/PCBM + PC/Al | $1.8 \times 10^{-5}$ | 25 | $10^2$ |

The above table 3 shows average device characteristics of organic OFET fabricated with and without the use of the PC polymer additive.

Figure 5:
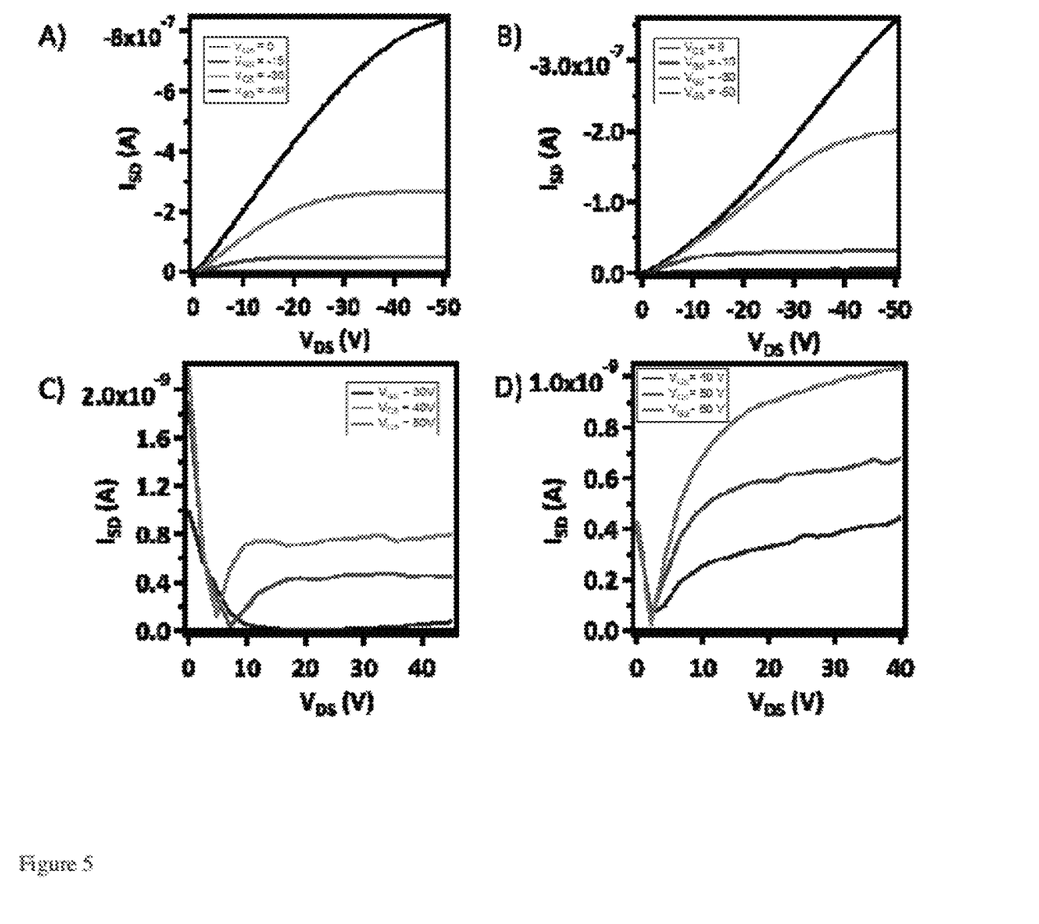
FIG. 5 shows output curves of representative organic TFTs devices fabricated with and without the use of the PC polymer additive.

FIG. 5 show the output curves of representative devices of the four device types in above Table 3.

Conclusion for OFET Experiments:

Adding the PC binder to both p-type and n-type materials resulted in workable transistors, comparable to the same transistors without the PC binder. This shows that a decomposable binder material can aid in solution processing of small molecule transistors while still retaining device characteristics.

References Which Are Hereby Incorporated By Reference In Their Entirety

1. F. Würthner, K. Meerholz, Chem. Eur. J. 2010, 16, 9366-9373.
2. X. Zhan, D. Zhu, Polym. Chem., 2010, 1, 409-419.
3. A. J. Heeger, Chem. Soc. Rev., 2010, 39, 2354-2371.
4. J. L. Delgado, P. -A. Bouit, S. Filippone, M Á. Herranza, Nazario Martín, Chem. Commun., 2010, 46, 4853-4865.
5. S. Günes, H. Neugebauer, N. S. Sariciftci, Chem. Rev. 2007, 107, 1324-1338.
6. C. Li, M. Liu, N. G. Pschirer, M. Baumgarten, K. Müllen, Chem. Rev. 2010, 110, 6817-6855.
7. Y. -J. Cheng, S. -H. Yang, C. -S. Hsu, Chem. Rev. 2009, 109, 5868-5923.
8. A. C. Mayer, S. R. Scully, B. E. Hardin, M. W. Rowell, M. D. McGehee, Materials Today 2007, 10, 28.
9. Y. Sato, T. Niinomi, M. Hashiguchi, Y. Matsuo, E. Nakamura P. SPIE. 2007, 6656.
10. Y. Sato, T. Niinomi, Y. Abe, Y. Matsuo, E. Nakamura P. SPIE. 2008, 7052.
11. Y. Matsuo, Y. Sato, T. Niinomi, I. Soga, H. Tanaka, E. Nakamura, J. Am. Chem. Soc. 2009, 131, 16048.
12. M. Singh, H. M. Haverinen, P. Dhagat, G. E. Jabbour, Adv. Mater. 2010, 22, 673.
13. Y. Chang, S. Tseng, C. Chen, H. Meng, E. Chen, S. Horng, C. Hsu, Organic Electronics 2009, 10, 741.
14. V. Marin, E. Holder, M. M. Wienk, E. Tekin, D. Kozodaev, U. S. Schubert, Macromol. Rapid Commun. 2005, 26, 319.
15. E. Holder, B. M. W. Langeveld, U. S. Schubert, Adv. Mater. 2005, 17, 1109.
16. A. R. Murphy and J. M. J. Fré chet, Chem. Rev. 2007, 107, 1066-1096.
17. H. N. Tsao, K. Müllen, Chem. Soc. Rev., 2010, 39, 2372-2386.
18. Y. Yamashita, Sci. Technol. Adv. Mater. 10 (2009) 024313 (9 pp).
19. B. J. Jung, N. J. Tremblay, M. -L. Yeh, H. E. Katz, Chem. Mater., DOI:10.1021/cm102296d
20. A. C. Grimsdale, K. L. Chan, R. E. Martin, P. G. Jokisz, A. B. Holmes, Chemical Reviews, 2009, 109, 897-1091.
21. J. Kido, Y. Okamoto, Chem. Rev. 2002, 102, 2357-2368.
22. S. -C. Lo, P. L. Burn, Chem. Rev. 2007, 107, 1097-1116.
23. Y. Shirota, H. Kageyama, Chem. Rev. 2007, 107, 953-1010.
24. K. Walzer, B. Maennig, M. Pfeiffer, K. Leo, Chem. Rev. 2007, 107, 1233-1271.
25. X. Chen, Z. Chen, Y. Zhang, Macromolecules, 1991, 24, 5305.
26. O. Vogl, J. of Poly. Sci., Part A, 1964, Vol. 2, 4591-4606.
27. S. Ito, T. Murashima, H. Uno, N. Ono, Chem. Commun., 1998 1661.
28. S. Ito, N. Ono, S. Aramaki, JP2008100993.
29. T. Okujima, Y. Hashimoto, G. Jin, H. Yamada, H. Uno, N. Ono, Tetrahedron 64, 2008, 2405e2411.
30. S. Aramaki, J. Mizuguchi, Acta Crystallogr E Struct Rep Online 2003, 59, 1556-1558.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. A method of fabricating an organic device comprising
   providing a first solution comprising an organic semiconductor compound or a precursor compound thereof, a solvent and a decomposable polymer additive, wherein the organic semiconductor compound or the precursor compound thereof, and the decomposable polymer additive are dissolved in the first solution;
   casting said first solution; and
   removing at least 80% of the polymer additive by decomposing the polymer additive into volatile small molecules.

2. The method of claim 1, wherein the polymer additive is decomposed by radiation or heating the casted first solution to a temperature at or above the decomposition temperature of the polymer additive.

3. The method of claim 2, wherein the decomposition temperature of the polymer additive is 400° C. or lower.

4. The method of claim 3, wherein the polymer additive is either a linear or block copolymer.

5. The method of claim 4, wherein the polymer additive is selected from the group consisting of polyethers, polyacrylates, polyisocyanurates, aliphatic polycarbonates, polyethylene carbonates, polyesters, polysulfones and polystyrene or poly (αmethyl styrene).

6. The method of claim 4, wherein the polymer additive is selected from the group consisting of poly carbonate, polyphenylene oxide, poly (methyl methacrylate), poly (4-vinyl phenol), poly (4-vinyl pyridine), polyaldehyde, and poly(lactide-co-glycolide).

7. The method of claim 1, wherein the polymer additive of claim 1 produces a larger viscosity value of the first solution than that of the solution without the polymer by at least 0.2 cps.

8. The method of claim 6, wherein the poly carbonate has the following structure:

where R is bivalent and R is an alkanediyl, alkenediyl or alkynediyl group with less than 10 carbon atoms.

9. The method of claim 1, wherein said organic semiconductor compound or said precursor compound thereof is a compound with a molecular weight less than or equal to 2000.

10. The method of claim 4, wherein said organic semiconductor compound or said precursor compound thereof is a porphyrin or a phthalocyanine.

11. The method of claim 1, wherein the organic semiconductor compound is a polymer.

12. The method of claim 6, wherein the polymer is selected from the group consisting of P3HT, MEH-PPV, PBTTT, PDBTTT and PCDTBT.

13. The method of claim 1, wherein the organic semiconductor precursor compound is the following compound:

where Y1-Y4 are H or alkyl group; R1-R4 are H, alkyl group or aryl group, F, or Cl; Z1a-Z4b are H, or alkyl group; and M is bivalent metal.

14. The method of claim 1, wherein the organic semiconductor precursor compound is 1,4:8,11:15,18:22,25-tetraethano-29H,31H-tetrabenzo[b,g,l,q]porphyrin.

15. The method of claim 1, wherein the organic semiconductor compound is selected from the group consisting of a porphyrin, a phthalocyanine, and derivatives of C60, C70, C76, C80 and C84.

16. The method of claim 9, wherein the PCBNB, PCBM, and SIMEF derivatives of C60, C70, C76, C80 and C84 are selected.

17. The method of claim 1, wherein the device is coated with benzoporphyrin prior to casting said first solution.

18. The method of claim 1, further comprising casting a second solution, wherein the second solution comprises a second compound selected from a group consisting of C60, C70, C76, C80, C84, and PCBNB, PCBM, and SIMEF derivatives of C60, C70, C76, C80 and C84.

19. The method of claim 1, wherein the first solution can be effectively deposited on said device using inkjet printing and slot or blade coating.

20. An organic thin film transistor made according to the methods of claim 9.

21. A photovoltaic device made according to the method of claim 12.

22. A composition comprising
an organic semiconductor compound, or a precursor compound thereof, and a polymer additive, wherein at least 80% of the polymer additive is capable of decomposing into gas upon heating, wherein the organic semiconductor precursor is 1,4:8,11:15,18:22,25-tetraethano-29H, 31H-tetrabenzo [b,g,l,q]porphyrin, or one of the following compounds with the following formula:

where Y1-Y4 are H or alkyl group; R1-R4 are H, alkyl group or aryl group, F, or Cl; Z1a-Z4b are H, or alkyl group; and M is bivalent metal.

23. A method of fabricating an organic device comprising providing a first solution comprising:
an organic semiconductor compound or a precursor compound thereof,
a solvent and a decomposable polymer additive, wherein:
the organic semiconductor compound or the precursor compound thereof, and the decomposable polymer additive are dissolved in the first solution; and
the decomposable polymer additive is selected for an ability to increase the viscosity of the first solution;
casting said first solution; and
removing at least 80% of the polymer additive by decomposing the polymer additive into volatile small molecules.

24. A method of fabricating an organic device comprising:
providing a first solution comprising an organic semiconductor compound or a precursor compound thereof, a solvent and a decomposable polymer additive, wherein:
the organic semiconductor compound or the precursor compound thereof, and the decomposable polymer additive are dissolved in the first solution; and
the decomposable polymer additive comprises a poly carbonate;
casting said first solution; and
removing at least 80% of the polymer additive by decomposing the polymer additive into volatile small molecules.

* * * * *